United States Patent
Samain et al.

(10) Patent No.: US 6,391,292 B1
(45) Date of Patent: May 21, 2002

(54) HAIRSTYLING COMPOSITION COMPRISING A POLYMER WITH PARTICULAR CHARACTERISTICS AND AN IONIC FILM FORMING POLYMER

(75) Inventors: Henri Samain, Bièvres; Christine Dupuis, Paris, both of (FR)

(73) Assignee: L'Oréal S.A., Paris (FR)

( * ) Notice: Subject to any disclaimer, the term of this patent is extended or adjusted under 35 U.S.C. 154(b) by 0 days.

(21) Appl. No.: 09/600,975

(22) PCT Filed: Nov. 18, 1999

(86) PCT No.: PCT/FR99/02831

§ 371 Date: Sep. 25, 2000

§ 102(e) Date: Sep. 25, 2000

(87) PCT Pub. No.: WO00/30594

PCT Pub. Date: Jun. 2, 2000

(30) Foreign Application Priority Data

Nov. 26, 1998 (FR) ................................. 98 14906

(51) Int. Cl.⁷ ............................. A61K 7/06; A61K 9/00
(52) U.S. Cl. ................ 424/70.11; 424/70.1; 424/70.12; 424/70.16; 424/47
(58) Field of Search ........................... 424/70.1, 70.11, 424/70.12, 70.16, 47

(56) References Cited

U.S. PATENT DOCUMENTS

| | | |
|---|---|---|
| 2,047,398 A | 7/1936 | Voss et al. |
| 2,723,248 A | 11/1955 | Wright |
| 3,716,633 A | 2/1973 | Viout et al. |
| 3,836,537 A | 9/1974 | Boerwinkle |
| 3,946,749 A | 3/1976 | Papantoniou |
| 3,966,403 A | 6/1976 | Papantoniou et al. |
| 3,966,404 A | 6/1976 | Papantoniou et al. |
| 4,031,307 A | 6/1977 | DeMartino et al. |
| 4,128,631 A | 12/1978 | Lundmark et al. |
| 4,137,208 A | 1/1979 | Elliott |
| 4,165,367 A | 8/1979 | Chakrabarti |
| 4,282,203 A | 8/1981 | Jacquet et al. |
| 4,693,935 A | 9/1987 | Mazurek |
| 4,728,571 A | 3/1988 | Clemens et al. |
| 4,972,037 A | 11/1990 | Garbe et al. |
| 5,538,517 A | 7/1996 | Samain et al. |
| 6,248,316 B1 * | 6/2001 | Peffly et al. |

FOREIGN PATENT DOCUMENTS

| | | |
|---|---|---|
| DE | 23 30 956 | 1/1974 |
| DE | 43 16 242 | 11/1994 |
| EP | 0 080 976 | 6/1983 |
| EP | 0 412 704 | 2/1991 |
| EP | 0 412 707 | 2/1991 |
| EP | 0 582 152 | 2/1994 |
| EP | 0 619 111 | 10/1994 |
| EP | 0 637 600 | 2/1995 |
| EP | 0 648 485 | 4/1995 |
| EP | 0 751 162 | 1/1997 |
| EP | 0 656 021 | 10/1997 |
| FR | 1 222 944 | 6/1960 |
| FR | 1 564 110 | 4/1969 |
| FR | 1 580 545 | 9/1969 |
| FR | 2 077 143 | 10/1971 |
| FR | 2 265 781 | 10/1975 |
| FR | 2 265 782 | 10/1975 |
| FR | 2 350 384 | 12/1977 |
| FR | 2 357 241 | 2/1978 |
| FR | 2 393 573 | 1/1979 |
| FR | 2 439 798 | 5/1980 |
| FR | 1 400 366 | 4/1985 |
| FR | 2 743 297 | 7/1997 |
| FR | 2 750 047 | 12/1997 |
| GB | 0 839 805 | 6/1960 |
| JP | 05-017320 | * 1/1993 |
| JP | 07-145023 | * 6/1995 |
| WO | WO 93/23009 | 11/1993 |
| WO | WO 93/23446 | 11/1993 |
| WO | WO 94/01077 | 1/1994 |
| WO | WO 94/03510 | 2/1994 |
| WO | WO 95/00578 | 1/1995 |
| WO | WO 97/15275 | 5/1997 |
| WO | WO 98/19653 | 5/1998 |

OTHER PUBLICATIONS

BF Goodrich, "Avalure™ Film Forming Polymers for Personal Care Applications", TDS 248, Apr. 5, 1999, pp. 1–5.
English language Derwent Abstract of DE 43 16 242.
English language Derwent Abstract of EP 0 080 976.
English language Derwent Abstract of EP 0 637 600.
English language Derwent Abstract of EP 0 656 021.
English language Derwent Abstract of EP 0 751 162.
English language Derwent Abstract of FR 1 564 110.
English language Derwent Abstract of FR 2 077 143.
English language Derwent Abstract of FR 2 357 241.
English language Derwent Abstract of FR 2 743 297.
English language Derwent Abstract of FR 2 750 047.

* cited by examiner

Primary Examiner—Thurman K. Page
Assistant Examiner—Brian K. Seidlech
(74) Attorney, Agent, or Firm—Finnegan, Henderson, Farabow, Garrett & Dunner, L.L.P.

(57) ABSTRACT

The invention concerns a hairstyling composition comprising, in a cosmetically acceptable medium: (1) at least a polymer (A) selected such that the film obtained by drying of a mixture of said polymer (A) with ethanol or water, at room temperature and at a relative moisture content of 50% has a mechanical profile defined by at least: (i) an ultimate elongation rate ($\epsilon_r$) not less than 300%; (ii) a creep at 300 seconds ($R_{300}$) not less than 45%; and (iii) when the creep at 300 seconds ranges between 45 and 60%, the elongation is less than 1300%; (2) at least a film forming polymer (B) different from polymer (A) and selected among anionic, cationic or amphoteric film forming polymers. The invention also concerns a hairstyling or hair-fixing method using said composition and its use for formulating hairstyling products such as lacquers, sprays and foams for hairstyling and hair fixing.

38 Claims, No Drawings

HAIRSTYLING COMPOSITION COMPRISING A POLYMER WITH PARTICULAR CHARACTERISTICS AND AN IONIC FILM FORMING POLYMER

This application is a 371 of PCT/FR99/02831, filed Nov. 18, 1999.

A subject-matter of the invention is a styling composition comprising, in a cosmetically acceptable medium, at least one polymer (A) with specific characteristics and at least one polymer (B) chosen from anionic, cationic or amphoteric film-forming polymers. It is also targeted at a process for shaping or retaining the form of the hair using this composition and at its use in the formulation of styling products, such as lacquers, sprays or mousses, for the purpose of obtaining form retention or shaping of the hairstyle.

The most widespread hair products on the cosmetics market for fixing the hair are compositions to be sprayed as an aerosol or as a pump-action spray, such as lacquers, sprays or mousses, composed essentially of a solution, generally an alcoholic or aqueous/alcoholic solution, and of a water-soluble or alcohol-soluble film-forming polymer, as a mixture with various cosmetic adjuvants.

However, these hair formulations, such as mousses, gels and especially aerosol sprays and lacquers intended to retain the form of the hairstyle, still do not make it possible for the hairstyle to satisfactorily withstand the various natural movements of life, such as walking, head movements or gusts of wind.

The polymers used for the formulation of these hair products are anionic, amphoteric or non-ionic film-forming polymers which result in the formation of films having a more or less hard and brittle nature.

When the polymer is too brittle, the percentage of elongation at break measured on the film is low, that is to say generally of less than 2%, and the hold of the hairstyle over time is not assured.

To overcome this problem, these polymers have already been mixed with plasticizers, and more flexible and non-flaky coatings have already been obtained. However, these films are deformable and plastic, that is to say that, after deformation, they only recover their initial form to a very small extent. While the hold of the hairstyle is improved, it is still not satisfactory since the form of the hairstyle changes over time.

More satisfactory results in terms of hold have been obtained with compositions comprising a combination of film-forming polymers, such as, for example, a cellulose polymer and an acrylic polymer. However, these compositions are still not entirely satisfactory, insofar as the hair loses some of its natural cosmetic properties.

There is therefore a search for cosmetic compositions for form retention of and/or fixing the hairstyle which provide the hair with good cosmetic properties, in particular good disentangling, softness and a pleasant appearance, in addition to fixing which lasts.

Surprisingly and unexpectedly, the Applicant Company has discovered that it is impossible to overcome the technical problems mentioned above by using certain specific combinations of polymers.

A subject-matter of the invention is a styling composition comprising, in a cosmetically acceptable medium:

(1) at least one polymer (A) chosen so that a film obtained by drying a mixture of this polymer (A) with ethanol or water, at room temperature and at a relative humidity level of 50%, exhibits a mechanical profile defined by at least:

(i) a degree of elongation at break ($\epsilon_b$) of greater than or equal to 300%;
(ii) a recovery at 300 seconds ($R_{300}$) of greater than or equal to 45%; and
(iii) when the recovery at 300 seconds is between 45 and 60%, then the elongation is less than 1300%;

(2) at least one film-forming polymer (B), other than the polymer (A), chosen from anionic, cationic or amphoteric film-forming polymers.

Another subject-matter of the present invention relates to a process for shaping or retaining the form of the hairstyle comprising the use of this composition.

Yet another subject-matter of the present invention relates to the use of this composition in the manufacture of hair cosmetic compositions for the purpose of obtaining form retention or shaping of the hairstyle.

The polymers (A) particularly targeted by the present invention are those distributed by Goodrich under the name Avalure AC 315® and V29®.

Within the meaning of the present invention, the term "film obtained by drying at room temperature (22±2° C.) and at a relative humidity level of 50% ±5%" is understood to mean the film obtained under these conditions starting from a mixture comprising 6% of active material (a.m.) of polymer A with ethanol or water, the amount of mixture being adjusted in order to obtain, in a Teflon matrix, a film with a thickness of 500±50 μm. The drying is continued until the weight of the film no longer changes, which represents approximately 12 days. The polymers A which are soluble or partially soluble in ethanol are tested in ethanol. The other polymers are tested in water, in the dissolved or dispersed form.

Within the meaning of the present invention, the degree of elongation at break and the degree of recovery are evaluated by means of the tests described below.

In order to carry out the tensile tests, the film is cut into rectangular test specimens with a length of 80 mm and a width of 15 mm.

The tests are carried out on a device, sold under the name Lloyd or sold under the name Zwick, under the same temperature and humidity conditions as for the drying, that is to say a temperature of 22±2° C. and a relative humidity level of 50±5%.

The test specimens are drawn at the rate of 20 mm/min and the distance between the jaws is 50±1 mm.

The following procedure is used to determine the instantaneous recovery ($R_i$):

the test specimen is drawn by 150% ($\epsilon_{max}$), that is to say 1.5 times its initial length ($l_0$)

the stress is released at a return rate equal to the tensile rate, i.e. 20 mm/min, and the elongation of the test specimen is measured as a percentage after returning to zero load ($\epsilon_i$).

The instantaneous recovery as a % ($R_i$) is given by the formula below:

$$R_i = ((\epsilon_{max} - \epsilon_i)/\epsilon_{max}) \times 100$$

In order to determine the recovery at 300 seconds, the test specimen which has been subjected to the preceding operations is maintained at zero stress for an additional 300 seconds and its degree of elongation is measured as a percentage ($\epsilon_{300}$)

The recovery at 300 second as a % ($R_{300}$) is given by the formula below:

$$R_{300} = ((\epsilon_{max} - \epsilon_{300})/\epsilon_{max}) \times 100$$

The cationic, anionic or amphoteric film-forming polymers (B) which can be used in accordance with the invention are described below.

The cationic film-forming polymers which can be used according to the present invention are preferably chosen from polymers comprising primary, secondary, tertiary and/or quaternary amine groups forming part of the polymer chain or directly bonded to the latter and having a molecular weight of between 500 and approximately 5,000,000 and preferably between 1000 and 3,000,000.

Mention may more particularly be made, among these polymers, of the following cationic polymers:

(1) homopolymers or copolymers derived from acrylic or methacrylic esters or amides comprising at least one of the units of following formulae:

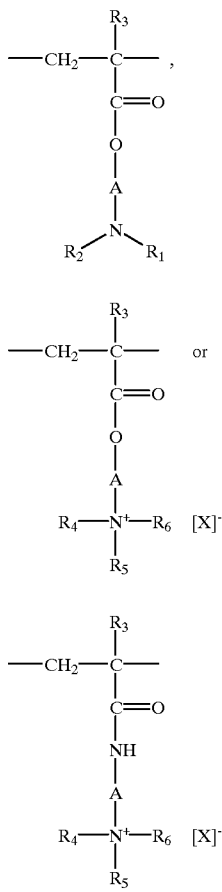

in which:
- $R_3$ denotes a hydrogen atom or a $CH_3$ radical;
- A is a linear or branched alkyl group comprising 1 to 6 carbon atoms or a hydroxyalkyl group comprising 1 to 4 carbon atoms;
- $R_4$, $R_5$ and $R_6$, which are identical or different, represent an alkyl group having from 1 to 18 carbon atoms or a benzyl radical;
- $R_1$ and $R_2$ represent hydrogen or an alkyl group having from 1 to 6 carbon atoms;
- X denotes a methyl sulphate anion or a halide, such as chloride or bromide.

The copolymers of the family (1) additionally comprise one or more units deriving from comonomers which can be chosen from the family of acrylamides, methacrylamides, diacetone acrylamides, acrylamides and methacrylamides substituted on the nitrogen by lower alkyls, acrylic or methacrylic acids and their esters, vinyllactams, such as vinylpyrrolidone or vinyl-caprolactam, or vinyl esters.

Thus, mention may be made, among these copolymers of the family (1), of:

- copolymers of acrylamide and of dimethylaminoethyl methacrylate quaternized with dimethyl sulphate or with a dimethyl halide, such as that sold under the name Hercofloc by the company Hercules,
- copolymers of acrylamide and of methacryloyloxyethyltrimethylammonium chloride which is disclosed, for example, in Patent Application EP-A-080,976 and sold under the name Bina Quat P 100 by the company Ciba-Geigy,
- the copolymer of acrylamide and of methacryloyloxyethyltrimethylammonium methyl sulphate sold under the name Reten by the company Hercules,
- optionally quaternized vinylpyrrolidone/dialkylaminoalkyl acrylate or methacrylate copolymers, such as the products sold under the name "Gafquat" by the company ISP, such as, for example, "Gafquat 734" or "Gafquat 755", or the products named "Copolymer 845, 958 and 937". These polymers are disclosed in detail in French Patents 2,077,143 and 2,393,573,
- dimethylaminoethyl methacrylate/vinylcaprolactam/vinylpyrrolidone terpolymers, such as the product sold under the name Gaffix VC 713 by the company ISP,
- and the quaternized dimethylaminopropyl methacrylamide/vinylpyrrolidone copolymer, such as the product sold under the name "Gafquat HS 100" by the company ISP.

(2) quaternized polysaccharides, disclosed more particularly in U.S. Pat. Nos. 3,589,578 and 4,031,307, such as guar gums comprising cationic trialkylammonium groups.

Such products are sold in particular under the trade names Jaguar C13 S, Jaguar C 15 and Jaguar C 17 by the company Meyhall.

(3) quaternary copolymers of vinylpyrrolidone and of vinylimidazole, such as the products sold by BASF under the name Luviquat FC;

(4) chitosans or their salts; the salts which can be used are in particular chitosan acetate, lactate, glutamate, gluconate or pyrrolidonecarboxylate.

Mention may be made, among these compounds, of the chitosan having a degree of deacetylation of 90.5% by weight sold under the name Kytan Crude Standard by the company Aber Technologies or the chitosan pyrrolidonecarboxylate sold under the name Kytamer PC by the company Amerchol.

The anionic film-forming polymers generally used are polymers comprising groups derived from carboxylic, sulphonic or phosphoric acid and have a molecular weight of between approximately 500 and 5,000,000.

1) The carboxyl groups are contributed by unsaturated mono- or dicarboxylic acid monomers such as those corresponding to the formula:

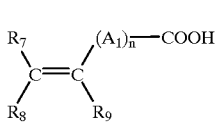

(II)

in which n is an integer from 0 to 10, $A_1$ denotes a methylene group, optionally bonded to the carbon atom of the unsaturated group or to the neighbouring methylene group when n is greater than 1 via a heteroatom, such as oxygen or sulphur, $R_7$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group.

In the abovementioned formula, a lower alkyl radical preferably denotes a group having 1 to 4 carbon atoms and in particular methyl and ethyl.

The preferred anionic film-forming polymers comprising carboxyl groups according to the invention are:

A) Homo- or copolymers of acrylic or methacrylic acid or their salts and in particular the products sold under the names Versicol E or K by the company Allied Colloid and Ultrahold by the company BASF. The copolymers of acrylic acid and of acrylamide sold in the form of their sodium salt under the names Reten 421, 423 or 425 by the Company Hercules or the sodium salts of polyhydroxy-carboxylic acids.

B) Copolymers of acrylic acid or methacrylic acid with a monoethylenic monomer, such as ethylene, styrene, vinyl esters or esters of acrylic or methacrylic acid, optionally grafted onto a polyalkylene glycol, such as polyethylene glycol, and optionally crosslinked. Such polymers are disclosed in particular in French Patent 1,222,944 and German Application 2,330,956, the copolymers of this type comprising, in their chain, an optionally N-alkylated and/or -hydroxyalkylated acrylamide unit, such as disclosed in particular in Luxembourgian Patent Applications 75370 and 75371 or provided under the name Quadramer by the Company American Cyanamid. Mention may also be made of copolymers of acrylic acid and of $C_1$–$C_4$ alkyl methacrylate and terpolymers of vinylpyrrolidone, of acrylic acid and of $C_1$–$C_{20}$ alkyl methacrylate, for example lauryl methacrylate, such as that sold by the company ISP under the name Acrylidone LM, and methacrylic acid/ethyl acrylate/tert-butyl acrylate terpolymers, such as the product sold under the name Luvimer 100 P by the company BASF.

C) Copolymers derived from crotonic acid, such as those comprising, in their chain, vinyl acetate or propionate units and optionally other monomers, such as allyl or methallyl esters, vinyl ether or vinyl ester of a linear or branched saturated carboxylic acid comprising a long hydrocarbonaceous chain, such as those comprising at least 5 carbon atoms, it optionally being possible for these polymers to be grafted and crosslinked, or alternatively a vinyl, allyl or methallyl ester of an α- or β-cyclic carboxylic acid. Such polymers are disclosed, inter alia, in French Patents 1,222,944, 1,580,545, 2,265,782, 2,265, 781, 1,564,110 and 2,439,798. Commercial products coming within this class are the Resins 28-29-30, 26-13-14, and 28-13-10 sold by the company National Starch.

D) Copolymers derived from $C_4$–$C_8$ monounsaturated carboxylic acids or anhydrides chosen from:

copolymers comprising (i) one or more maleic, fumaric or itaconic acids or anhydrides and (ii) at least one monomer chosen from vinyl esters, vinyl ethers, vinyl halides, phenylvinyl derivatives, or acrylic acid and its esters, the anhydride functional groups of these copolymers optionally being monoesterified or monoamidated; such polymers are disclosed in particular in U.S. Pat. Nos. 2,047,398, 2,723,248 and 2,102,113 and Patent GB 839,805 and in particular those sold under the names Gantrez AN or ES by the company ISP.

copolymers comprising (i) one or more maleic, citraconic or itaconic anhydrides and (ii) one or more monomers chosen from allyl or methallyl esters, optionally comprising one or more acrylamide, methacrylamide, α-olefin, acrylic or methacrylic ester, acrylic or methacrylic acid, or vinylpyrrolidone groups in their chain, the anhydride functional groups of these copolymers optionally being monoesterified or monoamidated.

These polymers are, for example, disclosed in French Patents 2,350,384 and 2,357,241 of the Applicant Company.

E) Polyacrylamides comprising carboxylate groups.

The polymers comprising sulpho groups are polymers comprising vinylsulphonic, styrenesulphonic, naphthalenesulphonic or acrylamidoalkylsulphonic units.

These polymers can in particular be chosen from:

salts of polyvinylsulphonic acid having a molecular weight of between approximately 1000 and 100,000, as well as copolymers with an unsaturated comonomer, such as acrylic or methacrylic acids and their esters as well as acrylamide or its derivatives, vinyl ethers and vinylpyrrolidone.

salts of polystyrenesulphonic acid, [lacuna] the sodium salts having a molecular weight of approximately 500, 000 and of approximately 100,000 sold respectively under the names Flexan 500 and Flexan 130 by National Starch. These compounds are disclosed in Patent FR 2,198,719.

salts of polyacrylamidesulphonic acids, [lacuna] those mentioned in U.S. Pat. No. 4,128,631 and more particularly the polyacrylamidoethylpropanesulphonic acid sold under the name Cosmedia Polymer HSP 1180 by Henkel.

According to the invention, the anionic film-forming polymers are preferably chosen from acrylic acid copolymers, such as the acrylic acid/ethyl acrylate/N-tert-butylacrylamide terpolymer sold under the name Ultrahold Strong by the company BASF, copolymers derived from crotonic acid, such as the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, polymers derived from maleic, fumaric or itaconic acids or anhydrides with vinyl esters, vinyl ethers, vinyl halides, phenylvinyl derivatives, or acrylic acid and its esters, such as the monoesterified methyl vinyl ether/maleic anhydride copolymer sold under the name Gantrez ES 425 by the company ISP, copolymers of methacrylic acid and of methyl methacrylate sold under the name Eudragit L by the company Rohm Pharma, the copolymer of methacrylic acid and of ethyl acrylate sold under the name Luvimer MAEX or MAE by the company BASF, the vinyl acetate/crotonic acid copolymer sold under the name Luviset CA 66 by the company BASF and the vinyl acetate/crotonic acid copolymer grafted by polyethylene glycol [lacuna] under the name Aristoflex A by the company BASF.

The most particularly preferred anionic film-forming polymers are chosen from the monoesterified methyl vinyl ether/maleic anhydride copolymer sold under the name Gantrez ES 425 by the company ISP, the acrylic acid/ethyl acrylate/N-tert-butylacrylamide terpolymer sold under the name Ultrahold Strong by the company BASF, the copolymers of methacrylic acid and of methyl methacrylate sold under the name Eudragit L by the company Rohm Pharma, the vinyl acetate/vinyl tert-butylbenzoate/crotonic acid terpolymers and the crotonic acid/vinyl acetate/vinyl neododecanoate terpolymers sold under the name Resin 28-29-30 by the company National Starch, the copolymer of methacrylic acid and of ethyl acrylate sold under the name Luvimer MAEX or MAE by the company BASF or the vinylpyrrolidone/acrylic acid/lauryl methacrylate terpolymer sold under the name Acrylidone LM by the company ISP.

The amphoteric film-forming polymers which can be used in accordance with the invention can be chosen from polymers comprising B and C units distributed randomly in the polymer chain, where B denotes a unit deriving from a monomer comprising at least one basic nitrogen atom and C denotes a unit deriving from an acidic monomer comprising one or more carboxyl or sulpho groups or else B and C can denote groups deriving from zwitterionic carboxybetaine or sulphobetaine monomers; B and C can also denote a cationic polymer chain comprising primary, secondary, tertiary or quaternary amine groups, in which at least one of the amine groups carries a carboxyl or sulpho group connected via a hydrocarbonaceous radical, or else B and C form part of a chain of a polymer comprising an α,β-dicarboxy-ethylene unit, one of the carboxyl groups of which has been reacted with a polyamine comprising one or more primary or secondary amine groups.

The most particularly preferred amphoteric film-forming polymers corresponding to the definition given above are chosen from the following polymers:

1) polymers resulting from the copolymerization of a monomer derived from a vinyl compound carrying a carboxyl group, such as more particularly acrylic acid, methacrylic acid, maleic acid or α-chloracrylic acid, and of a basic monomer derived from a substituted vinyl compound comprising at least one basic atom, such as more particularly dialkylaminoalkyl methacrylate and acrylate or dialkylaminoalkylmethacrylamide and -acrylamide. Such compounds are dislosed in U.S. Pat. No. 3,836,537.

2) polymers comprising units deriving:
   a) from at least one monomer chosen from acrylamides or methacrylamides substituted on the nitrogen by an alkyl radical,
   b) from at least one acidic comonomer comprising one or more reactive carboxyl groups, and
   c) from at least one basic comonomer, such as esters comprising primary, secondary, tertiary and quaternary amine substituents of acrylic and methacrylic acids and the quaternization product of dimethylaminoethyl methacrylate with dimethyl or diethyl sulphate.

The more particularly preferred N-substituted acrylamides or methacrylamides according to the invention are the groups in which the alkyl radicals comprise from 2 to 12 carbon atoms and more particularly N-ethylacrylamide, N-tert-butylacrylamide, N-tert-octylacrylamide, N-octylacrylamide, N-decylacrylamide or N-dodecylacrylamide, and the corresponding methacrylamides.

The acidic comonomers are more particularly chosen from acrylic, methacrylic, crotonic, itaconic, maleic or fumaric acids and alkyl monoesters having 1 to 4 carbon atoms of maleic or fumaric acids or anhydrides.

The preferred basic comonomers are aminoethyl, butylaminoethyl, N,N'-dimethylaminoethyl or N-tert-butylaminoethyl methacrylates.

Use is particularly made of the copolymers for which the CTFA name (4th Ed., 1991) is Octylacrylamide/acrylates/butylaminoethyl methacrylate copolymer, such as the products sold under the name Amphomer or Lovocryl 47 by the company National Starch.

(3) partially or completely alkylated and crosslinked polyaminoamides deriving from polyaminoamides of general formula:

(III)

in which $R_{10}$ represents a divalent radical derived from a saturated dicarboxylic acid, from an aliphatic mono- or dicarboxylic acid comprising an ethylenic double bond, from an ester of a lower alkanol having 1 to 6 carbon atom of these acids, or from a radical deriving from the addition of any one of the said acids with a bisprimary or bissecondary amine, and Z denotes a radical of a bisprimary, mono- or bissecondary polyalkylenepolyamine and preferably represents:

a) in the proportions of 60 to 100 mol %, the radical

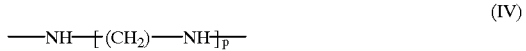

(IV)

where x=2 and p=2 or 3, or else x=3 and p=2 this radical deriving from diethylenetriamine, triethylenetetraamine or dipropylenetriamine;

b) in the proportions of 0 to 40 mol %, the above radical (IV), in which x=2 and p=1 and which derives from ethylenediamine, or the radical deriving from piperazine:

c) in the proportions of 0 to 20 mol %, the radical $-NH-(CH_2)_6-NH-$ deriving from hexamethylenediamine, these polyaminoamines being crosslinked by addition of a bifunctional crosslinking agent chosen from epihalohydrins, diepoxides, dianhydrides or bisunsaturated derivatives, by means of 0.025 to 0.35 mol of crosslinking agent per amine group of the polyaminoamide, and alkylated by reaction with acrylic acid, chloracetic acid or an alkanesultone or their salts.

The saturated carboxylic acids are preferably chosen from acids having 6 to 10 carbon atoms, such as adipic, 2,2,4-trimethyladipic or 2,4,4-trimethyladipic, or terephthalic acid, and the acids comprising an ethylenic double bond, such as, for example, acrylic, methacrylic or itaconic acids.

The alkanesultones used in the alkylation are preferably propane- or butanesultone and the salts of the alkylating agents are preferably the sodium or potassium salts.

(4) polymers comprising zwitterionic units of formula:

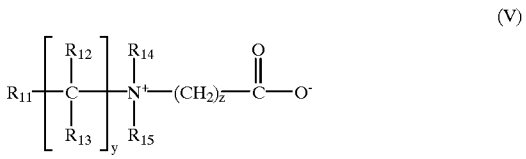

(V)

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and $R_{14}$ and $R_{15}$ represent a hydrogen atom or an alkyl radical such that the sum of the carbon atoms in $R_{14}$ and $R_{15}$ does not exceed 10.

The polymers comprising such units can also comprise units derived from non-zwitterionic monomers, such as dimethyl- or diethylaminoethyl acrylate or methacrylate or alkyl acrylates or methacrylates, acrylamides or methacrylamides, or vinyl acetate.

Mention may be made, by way of example, of the methyl methacrylate/methyl dimethylcarboxymethylammonioethyl methacrylate copolymer, such as the product sold under the name Diaformer Z301 by the company Sandoz.

(5) polymers derived from chitosan comprising monomer units corresponding to the following formulae:

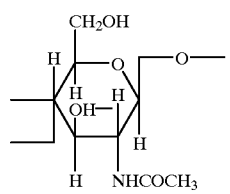

(D)

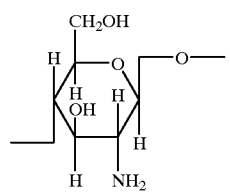

(E)

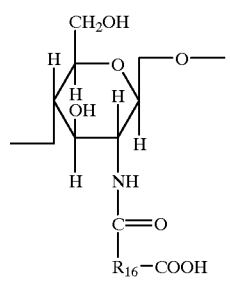

(F)

the unit D being present in proportions of between 0 and 30%, the unit E in proportions of between 5 and 50% and the unit F in proportions of between 30 and 90%, it being understood that, in this unit F, $R_{16}$ represents a radical of formula:

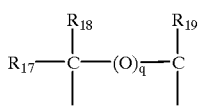

in which, if q=0, $R_{17}$, $R_{18}$ and $R_{19}$, which are identical or different, each represent a hydrogen atom, a methyl, hydroxyl, acetoxy or amino residue, a monoalkylamine residue or a dialkylamine residue, optionally interrupted by one or more nitrogen atoms and/or optionally substituted by one or more amine, hydroxyl, carboxy, alkylthio or sulpho groups, or an alkylthio residue in which the alkyl group carries an amino residue, at least one of the $R_{17}$, $R_{18}$ and $R_{19}$ radicals being, in this case, a hydrogen atom; or, if q=1, $R_{17}$, $R_{18}$ and $R_{19}$ each represent a hydrogen atom, and the salts formed by these compounds with bases or acids.

(6) polymers derived from the N-carboxyalkylation of chitosan, such as the N-(carboxymethyl)chitosan or the N-(carboxybutyl)chitosan sold under the name "Evalsan" by the company Jan Dekker.

(7) polymers corresponding to the general formula (VI), for example disclosed in French Patent 1,400,366:

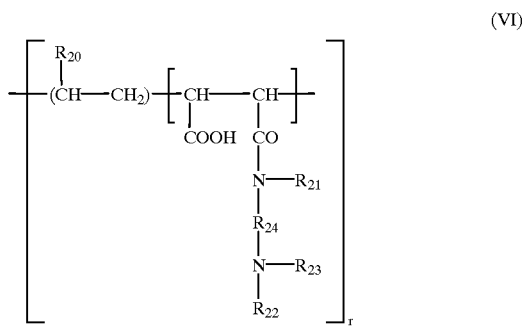

(VI)

in which $R_{20}$ represents/a hydrogen atom or a $CH_3O$ $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl and $R_{23}$ denotes a lower alkyl radical such as methyl or ethyl or a radical corresponding to the formula: $-R_{24}-N(R_{22})_2$, $R_{24}$ representing a $-CH_2-CH_2-$, $-CH_2-CH_2-CH_2-$ or $-CH_2-CH(CH_3)-$ group and $R_{22}$ having the meanings mentioned above, and the higher homologues of these radicals comprising up to 6 carbon atoms.

(8) amphoteric polymers of the $-D-X-D-X-$ type chosen from:
  a) polymers obtained by reaction of chloracetic acid or sodium chloracetate with compounds comprising at least one unit of formula:

$$-D-X-D-X-D- \qquad (VII')$$

where D denotes a radical

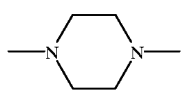

and X denotes the symbol E or E', E or E', which are identical or different, denote a bivalent radical which is a straight- or branched-chain alkylene radical comprising up to 7 carbon atoms in the main chain which is unsubstituted or substituted by hydroxyl groups and which can additionally comprise oxygen, nitrogen or sulphur atoms or 1 to 3 aromatic and/or heterocyclic rings; the oxygen, nitrogen and sulphur atoms being present in the form of ether, thioether, sulphoxide, sulphone, sulphonium, alkylamine or alkenylamine groups or hydroxyl, benzylamine, amine oxide, quaternary ammonium, amide, imide, alcohol, ester and/or urethane groups.

b) polymers of formula:

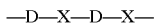 (VII')

where D denotes a radical

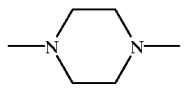

and X denotes the symbol E or E' and E' at least once, E having the meaning indicated above and E' is a bivalent radical which is a straight- or branched-chain alkylene radical having up to 7 carbon atoms in the main chain which is substituted or unsubstituted by one or more hydroxyl radicals and which comprises one or more nitrogen atoms, the nitrogen atom being substituted by an alkyl chain optionally interrupted by an oxygen atom and necessarily comprising one or more carboxyl functional groups and one or more hydroxyl functional groups and betainized by reaction with chloracetic acid or sodium chloracetate.

(9) (C1–C5)alkyl vinyl ether/maleic anhydride copolymers which is partially modified by semiamidation with an N,N-dialkylaminoalkylamine, such as N,N-dimethylaminopropylamine, or by semiesterification with an N,N-dialkanolamine. These copolymers can also comprise other vinyl comonomers, such as vinylcaprolactam.

The particularly preferred amphoteric film-forming polymers according to the invention are those of the family (3), such as the copolymers with the CTFA name of Octylacrylamide/acrylates/butylaminoethyl methacrylate copolymer, such as the products sold under the names Amphomer, Amhomer LV 71 or Lovocryl 47 by the company National Starch, and those of the family (4), such as methyl methacrylate/methyl dimethylcarboxymethylammonioethyl methacrylate copolymer, for example sold under the name Diaformer Z301 by the company Sandoz.

According to the invention, it is also possible to use anionic film-forming polymers of grafted silicone type comprising a polysiloxane portion and a portion composed of a non-silicone organic chain, one of the two portions constituting the main chain of the polymer and the other being grafted onto the said main chain. These polymers are disclosed, for example, in Patent Applications EP-A-0,412,704, EP-A-0,412,707, EP-A-0,640,105 and WO 95/00578, EP-A-0,582,152 and WO 93/23009 and U.S. Pat. Nos. 4,693,935, 4,728,571 and 4,972,037.

Such polymers are, for example, the copolymers capable of being obtained by radical polymerization from the mixture of monomers composed of:

a) 50 to 90% by weight of tert-butyl acrylate;
b) 0 to 40% by weight of acrylic acid;
c) 5 to 40% by weight of silicone macromer of formula:

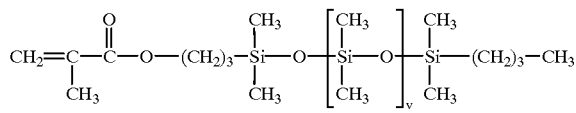

with v being a number ranging from 5 to 700, the percentages by weight being calculated with respect to the total weight of the monomers.

Other examples of grafted silicone polymers are in particular polydimethylsiloxanes (PDMSs) on which are grafted, via a connecting link of thiopropylene type, mixed polymer units of the poly(meth)acrylic acid type and of the poly(alkyl (meth)acrylate) type and polydimethylsiloxanes (PDMSs) on which are grafted, via a connecting link of thiopropylene type, polymer units of the poly(isobutyl (meth)acrylate) type.

Use may also be made, as film-forming polymers, of functionalized polyurethanes which may or may not comprise silicones.

The polyurethanes particularly targeted by the present invention are those disclosed in Patents EP 0,751,162, EP 0,637,600, FR 2,743,297 and EP 0,648,485, of which the Applicant Company is Proprietor, and Patents EP 0,656,021 or WO 94/03510 of the Company BASF and EP 0,619,111 of the Company National Starch.

In the compositions in accordance with the invention, the film-forming polymer or polymers (A) are preferably present at concentrations of between 0.05 and 20% by weight, more preferably of between 0.1 and 15% by weight and more preferably between 0.25 and 10% by weight with respect to the total weight of the composition.

In the compositions in accordance with the invention, the film-forming polymer or polymers (B) are preferably present at concentrations of between 0.05 and 20% by weight, more preferably of between 0.1 and 15% by weight and more preferably between 0.25 and 10% by weight with respect to the total weight of the composition.

The concentrations of polymers (A) and (B) are advantageously chosen so that the ratio of the concentration of polymer (A) to the concentration of polymer (B) is between 4000 and 0.002.

The cosmetically acceptable medium is preferably composed of water or one or more cosmetically acceptable solvents, such as alcohols or water/solvent(s) mixtures, these solvents preferably being $C_1$–$C_4$ alcohols.

Mention may be made, among these alcohols, of ethanol or isopropanol. Ethanol is particularly preferred.

The composition of the invention can also comprise at least one additive chosen from thickeners, surfactants, fragrances, preservatives, sunscreens, proteins, vitamins, non-fixing polymers and any other additive conventionally used in cosmetic compositions intended to be applied to the hair.

Of course, a person skilled in the art will take care to choose the optional compound or compounds to be added to the composition according to the invention so that the advantageous properties intrinsically attached to the composition in accordance with the invention are not, or not substantially, detrimentally affected by the envisaged addition.

These compositions can be packaged in various forms, in particular in pump-action sprays or in aerosol containers, in order to ensure application of the composition in vaporized form or in mousse form. Such packaging forms are indicated, for example, when it is desired to obtain a spray, a lacquer or a mousse for fixing or treating the hair. The compositions in accordance with the invention can also be provided in the form of creams, of gels, of emulsions, of lotions or of waxes.

When the composition according to the invention is packaged in aerosol form for the purpose of obtaining a lacquer or a mousse, it comprises at least one propellant which can be chosen from volatile hydrocarbons, such as n-butane, propane, isobutane, pentane, a chlorinated and/or fluorinated hydrocarbon and their mixtures. Use may also be made, as propellant, of carbon dioxide gas, nitrous oxide, dimethyl ether (DME), nitrogen or compressed air. Use may also be made of mixtures of propellants. Dimethyl ether is preferably used.

The propellant is advantageously present at a concentration of between 5 and 90% by weight with respect to the total weight of the composition in the aerosol device and more particularly at a concentration of between 10 and 60%.

The compositions in accordance with the invention can be applied to dry or wet hair.

The invention will be more fully illustrated with the help of the following nonlimiting example.

All the percentages are relative percentages by weight with respect to the total weight of the composition and a.m. means active material.

Use is made of the polymers indicated below:

| Avalure AC 315 | acrylic polymer sold by Goodrich |
| Amphomer | octylacrylamide/acrylates/butyl-aminoethyl methacrylate amphoteric polymer sold by the company National Starch |
| Luvitec VPI 55K72 | vinylpyrrolidone/vinylimidazole cationic polymer sold by BASF |
| Polymer X | crotonic acid/vinyl acetate/vinyl tert-butylate anionic polymer |
| VS80 | anionic polymer comprising a polysiloxane backbone grafted with non-silicone monomers |

EXAMPLE 5 styling compositions are prepared, all comprising Avalure AC315 as polymer (A).

One of the styling compositions is in accordance with the prior art and comprises ethyl cellulose as film-forming polymer (B). The other 4 styling compositions are in accordance with the present invention and comprise an amphoteric, anionic or cationic film-forming polymer.

The formulations prepared are summarized in Table 1 below.

TABLE 1

| | Composition 1 (prior art) | Composition 2 (invention) | Composition 3 (invention) | Composition 4 (invention) | Composition 5 (invention) |
|---|---|---|---|---|---|
| Avalure | 2.65% | 2.65% | 2.65% | 2.65% | 2.65% |
| Ethyl cellulose | 0.2% | — | — | — | — |
| Amphomer | — | 0.35% | — | — | — |
| Luvitec VP155 | — | — | 0.35% | — | — |
| Polymer X | — | — | — | 0.35% | — |
| VS80 | — | — | — | — | 0.35% |
| Ethanol | q.s. 100 | q.s. 100 | q.s. 100 | q.s. 100 | q.s. 100 |

Compositions 1 to 5, packaged as aerosols (composition, DME 35%), are applied to locks of eurochestnut hair with a length of 18 cm and a weight of 20 grams.

The softness and the ease of disentangling of the hair after application of these compositions to the hair are evaluated by means of a sensory test with a panel of 5 people. The grades attributed range from 0 (poor performance) to 50 (excellent performance). The disentangling evaluated is the ease with which the comb can be run through after a first disentangling in order to break the polymer/individual hair junctions. The results obtained are summarized in Table 2 below.

TABLE 2

| | Composition 1 (prior art) | Composition 2 (invention) | Composition 3 (invention) | Composition 4 (invention) | Composition 5 (invention) |
|---|---|---|---|---|---|
| Softness | 10 | 20 | 25 | 35 | 35 |
| Disentangling | 20 | 30 | 35 | 35 | 40 |

It results from this that the compositions in accordance with the present invention provide a markedly better performance in terms of softness and of disentangling than the compositions comprising a combination of polymers in accordance with the prior art.

What is claimed is:

1. A composition comprising:
   (1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:
      (i) a degree of elongation at break ($\epsilon_b$) of greater than or equal to 300%; and
      (ii) a degree of recovery at 300 seconds ($R_{300}$) of greater than or equal to 45%;
      with the proviso that when said degree of recovery at 300 seconds ranges from 45% to 60%, said degree of elongation is less than 1300%; and
   (2) at least one film-forming polymer (B), different from said at least one polymer (A), chosen from anionic film-forming polymers, cationic film-forming polymers, and amphoteric film-forming polymers.

2. A composition according to claim 1, wherein said at least one film-forming polymer (B) is chosen from cationic polymers comprising at least one group chosen from primary amine groups, secondary amine groups, tertiary amine groups, and quaternary amine groups.

3. A composition according to claim 1, wherein said at least one film-forming polymer (B) is chosen from cationic polymers, wherein said cationic polymers are chosen from:
   (1) homopolymers and copolymers of at least one monomer chosen from acrylic esters, methacrylic esters, acrylic amides, and methacrylic amides;

(2) quaternized polysaccharides;

(3) quaternized copolymers of vinylpyrrolidone and of vinylimidazole; and (4) chitosans and salts thereof.

4. A composition according to claim 3, wherein said at least one monomer comprises at least one unit of at least one of the following formulae:

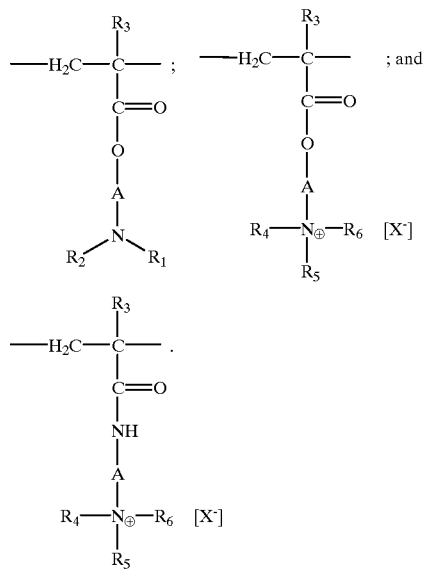

wherein:

$R_3$, which may be identical or different, are each chosen from hydrogen and $CH_3$ groups;

A, which may be identical or different, are each chosen from linear alkyl groups comprising from 1 to 6 carbon atoms, branched alkyl groups comprising from 1 to 6 carbon atoms, and hydroxyalkyl groups comprising from 1 to 4 carbon atoms;

$R_4$, $R_5$ and $R_6$, which may be identical or different, are each chosen from alkyl groups comprising from 1 to 18 carbon atoms and benzyl groups;

$R_1$ and $R_2$ which may be identical or different, are each chosen from hydrogen and alkyl groups comprising from 1 to 6 carbon atoms; and $X^-$ which may be identical or different, are each chosen from methyl sulphate anions and halide anions.

5. A composition according to claim 3, wherein said copolymers (1) may optionally further comprise at least one unit derived from comonomers, wherein said comonomers are chosen from acrylamides, methacrylamides, diacetone acrylamides, N-alkyl acrylamides, N-alkyl methacrylamides, acrylic acid, methacrylic acid, acrylic acid esters, methacrylic acid esters, vinyllactams, and vinyl esters.

6. A composition according to claim 3, wherein said copolymers (1) are chosen from:

(a) quaternized copolymers of acrylamide and of dimethylaminoethyl methacrylate;

(b) copolymers of acrylamide and of methacryloyloxyethyltrimethylammonium chloride;

(c) copolymers of acrylamide and of methacryloyloxyethyltrimethylammonium methyl sulphate;

(d) copolymers of (i) vinylpyrrolidone and (ii) dialkylaminoalkyl acrylate, optionally quaternized, and copolymers of (i) vinylpyrrolidone and (ii) dialkylaminoalkyl methacrylate, optionally quaternized;

(e) terpolymers of (i) dimethylaminoethyl methacrylate, (ii) vinylcaprolactam, and (iii) vinylpyrrolidone terpolymers; and (f) quaternized copolymers of (i) dimethylaminopropyl methacrylamide and (ii) vinylpyrrolidone.

7. A composition according to claim 1, wherein said anionic film-forming polymers are chosen from polymers derived from at least one monomer comprising at least one group chosen from carboxylic acid groups, sulphonic acid groups, phosphoric acid groups, and salts thereof.

8. A composition according to claim 7, wherein said at least one monomer comprising at least one group chosen from carboxylic acid groups is chosen from unsaturated monocarboxylic acid monomers of formula (II), unsaturated dicarboxylic acid monomers of formula (II), and salts thereof:

wherein:

n is an integer ranging from 0 to 10;

$A_1$ is chosen from methylene groups;

$R_7$ is chosen from hydrogen, phenyl groups, and benzyl groups;

$R_8$ is chosen from hydrogen, lower alkyl groups, and carboxyl groups; and $R_9$ is chosen from hydrogen, lower alkyl groups, $-CH_2COOH$ groups, phenyl groups, and benzyl groups;

wherein $A_1$ may optionally be bonded to the carbon atom of the unsaturated group or, when n is greater than 1, to the neighbouring methylene group via at least one heteroatom.

9. A composition according to claim 1, wherein said at least one film-forming polymer (B) is chosen from:

(a) homopolymers of at least one monomer chosen from acrylic acid, methacrylic acid, and salts thereof, and copolymers of at least one monomer chosen from acrylic acid, methacrylic acid, and salts thereof;

(b) copolymers of (i) at least one monomer chosen from acrylic acid, methacrylic acid, and salts thereof and (ii) at least one monomer chosen from monoethylenic monomers, optionally grafted onto a polyalkylene glycol, and optionally crosslinked;

(c) homopolymers and copolymers of crotonic acid;

(d) homopolymers and copolymers of at least one monomer chosen from $C_4$–$C_8$ monounsaturated carboxylic acids and $C_4$–$C_8$ monounsaturated carboxylic acid anhydrides, wherein the anhydride group of said $C_4$–$C_8$ monounsaturated carboxylic acid anhydrides may optionally be monoesterified or monoamidated; and (e) polyacrylamides comprising at least one carboxylate group.

10. A composition according to claim 1, wherein said at least one film-forming polymer (B) is chosen from:

(a) copolymers of acrylic acid;

(b) copolymers of crotonic acid;

(c) copolymers of (i) at least one monomer chosen from maleic acid, fumaric acid, itaconic acid, maleic anhydride, fumaric anhydride, and itaconic anhydride and (ii) at least one monomer chosen from vinyl esters, vinyl ethers, vinyl halides, phenylvinyl derivatives, acrylic acids, and acrylic acid esters;

(d) copolymers of methacrylic acid and of methyl methacrylate; and (e) copolymers of methacrylic acid and of ethyl acrylate.

11. A composition according to claim 10, wherein said copolymers of crotonic acid are chosen from (1) terpolymers of (i) vinyl acetate, (ii) vinyl tert-butylbenzoate, and (iii) crotonic acid, (2) terpolymers of (i) crotonic acid, (ii) vinyl acetate, and (iii) vinyl neododecanoate, (3) copolymers of (i) vinyl acetate and (ii) crotonic acid, and copolymers of (i) vinyl acetate and (ii) crotonic acid, grafted by polyethylene glycol.

12. A composition according to claim 1, wherein said at least one film-forming polymer (B) is chosen from amphoteric polymers, wherein said amphoteric polymers are chosen from polymers comprising at least one B unit and at least one C unit, wherein:

(a) said at least one B unit is chosen from units derived from at least one monomer comprising at least one basic nitrogen atom; and
said at least one C unit is chosen from units derived from at least one acidic monomer comprising at least one group chosen from carboxyl groups and sulpho groups;

(b) said at least one B and at least one C unit, which may be identical or different, are each chosen from groups derived from zwitterionic carboxybetaines and groups derived from sulphobetaine monomers;

(c) said at least one B unit and at least one C unit, which may be identical or different, are each chosen from cationic polymers comprising at least one group chosen from primary amine groups, secondary amine groups, tertiary amine groups, and quaternary amine groups, wherein at least one of said at least one group is substituted with a hydrocarbonaceous group comprising at least one group chosen from carboxyl groups and sulpho groups; or (d) said at least one B unit and at least one C unit, which may be identical or different, form part of a chain of at least one polymer which comprises at least one α,β-dicarboxy-ethylene unit, wherein at least one carboxyl group of said at least one polymer has been reacted with a polyamine comprising at least one amine group chosen from primary amine groups and secondary amine groups.

13. A composition according to claim 1, wherein said at least one film-forming polymer (B) is chosen from amphoteric polymers, wherein said amphoteric polymers are chosen from copolymers of (i) at least one monomer derived from at least one vinyl group which comprises at least one carboxyl group and (ii) at least one basic monomer derived from at least one substituted vinyl group which comprises at least one basic atom.

14. A composition according to claim 1, wherein said at least one film-forming polymer (B) is chosen from amphoteric polymers, wherein said amphoteric polymers are chosen from polymers derived from:

(a) at least one monomer chosen from N-alkyl acrylamides and N-alkyl methacrylamides;

(b) at least one acidic monomer comprising at least one reactive carboxyl group; and (c) at least one basic comonomer.

15. A composition according to claim 14, wherein said at least one basic comonomer is chosen from aminoethyl methacrylate, butylaminoethyl methacrylate, N,N'-dimethylaminoethyl methacrylate, and N-tert-butylaminoethyl methacrylate.

16. A composition according to claim 1, wherein said at least one film-forming polymer (B) is chosen from amphoteric polymers, wherein said amphoteric polymers are chosen from copolymers of (i) octylacrylamide, (ii) acrylates, and (iii) butylaminoethyl methacrylate.

17. A composition according to claim 1, wherein said at least one film-forming polymer (B) is chosen from amphoteric polymers, wherein said amphoteric polymers are chosen from partially alkylated crosslinked polyaminoamides derived from polyaminoamides of formula (III) and completely alkylated crosslinked polyaminoamides derived from polyaminoamides of formula (III):

wherein:

$R_{10}$ is chosen from divalent groups derived from at least one group chosen from saturated dicarboxylic acids, aliphatic monocarboxylic acids comprising at least one ethylenic double bond, aliphatic dicarboxylic acids comprising at least one ethylenic double bond, esters of alkanol groups comprising from 1 to 6 carbon atoms of said at least one group, and groups derived from addition of said at least one group with at least one amine chosen from bisprimary amines and bissecondary amines; and Z is chosen from divalent bisprimary polyalkylenepolyamines, divalent monosecondary polyalkylenepolyamines, and divalent bissecondary polyalkylenepolyamines.

18. A composition according to claim 1, wherein said at least one film-forming polymer (B) is chosen from amphoteric polymers, wherein said amphoteric polymers are chosen from polymers comprising at least one zwitterionic unit of formula (V):

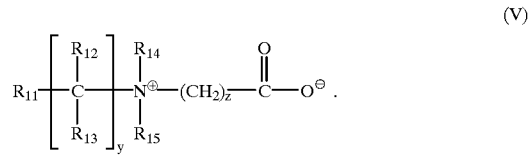

wherein:

$R_{11}$ is chosen from polymerizable unsaturated groups;

y and z, which may be identical or different, are each chosen from integers ranging from 1 to 3;

$R_{12}$ and $R_{13}$, which may be identical or different, are each chosen from hydrogen, methyl groups, ethyl groups, and propyl groups; and $R_{14}$ and $R_{15}$ are each chosen from hydrogen and alkyl groups, wherein the total number of carbon atoms in both $R_{14}$ and $R_{15}$ is less than or equal to 10.

19. A composition according to claim 1, wherein said at least one film-forming polymer (B) is chosen from amphoteric polymers, wherein said amphoteric polymers are chosen from polymers derived from chitosan comprising at least one unit having at least one of the following formulae, the acid salts thereof, and the base salts thereof:

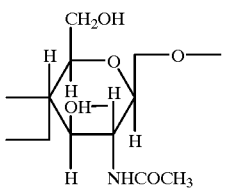

(D)

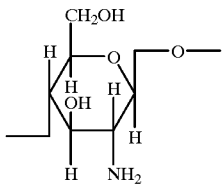

(E)

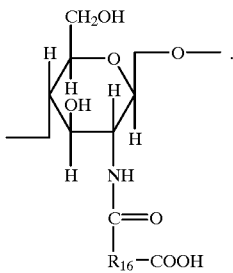

(F)

wherein said polymers comprise at least one unit D, if present, in a proportion ranging from 0% to 30% by weight relative to the total weight of said amphoteric polymers, at least one unit E, if present, in a proportion ranging from 5% to 50% by weight relative to the total weight of said amphoteric polymers, and at least one unit F, if present, in a proportion ranging from 30% to 90% by weight relative to the total weight of said amphoteric polymers, and further wherein $R_{16}$ is chosen from groups of formula:

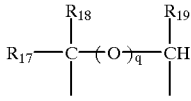

wherein:
q is equal to 0 or 1,
wherein if q is equal to 0, $R_{17}$, $R_{18}$ and $R_{19}$, which may be identical or different, are each chosen from hydrogen, methyl groups, hydroxyl groups, acetoxy groups, amino groups, monoalkylamine groups, and dialkylamine groups, optionally interrupted by at least one nitrogen atom and optionally substituted with at least one group chosen from amine groups, hydroxyl groups, carboxy groups, alkylthio groups, sulpho groups, and alkylthio groups wherein the alkyl group is substituted with at least one amino group, with the proviso that at least one of $R_{17}$, $R_{18}$ and $R_{19}$ is chosen from hydrogen; and
wherein if q is equal to 1, $R_{17}$, $R_{18}$ and $R_{19}$ which may be identical or different, are each chosen from hydrogen.

20. A composition according to claim 1, wherein said at least one film-forming polymer (B) is chosen from amphoteric polymers, wherein said amphoteric polymers are chosen from polymers derived from N-carboxyalkylation of chitosan.

21. A composition according to claim wherein said at least one film-forming polymer (B) is chosen from amphoteric polymers, wherein said amphoteric polymers comprise repeating units of formula (VI):

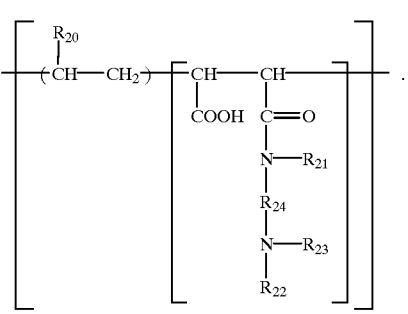

wherein:
$R_{20}$, which may be identical or different, are each chosen from hydrogen, $CH_3O$— groups, $CH_3CH_2O$— groups, and phenyl groups;
$R_{21}$, which may be identical or different, are each chosen from hydrogen and lower alkyl groups;
$R_{22}$, which may be identical or different, are each chosen from hydrogen and lower alkyl groups;
$R_{23}$, which may be identical or different, are each chosen from lower alkyl groups, groups of formula —$R_{24}$—$N(R_{22})_2$ wherein $R_{24}$ is chosen from —$CH_2$—$CH_2$— groups,
—$CH_2$—$CH_2$—$CH_2$— groups, —$CH_2$—$CH(CH_3)$— groups, and higher homologs thereof wherein said higher homologs comprise up to 6 carbon atoms.

22. A composition according to claim 1, wherein said at least one film-forming polymer (B) is chosen from amphoteric polymers, wherein said amphoteric polymers are chosen from polymers of formula —D—X—D—X—, and further wherein said polymers of formula —D—X—D—X— are chosen from:
(a) polymers obtained by reaction of (i) at least one of chloroacetic acid and sodium chloracetate with (ii) at least one compound comprising at least one unit of formula (VI):

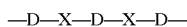 (VII)

wherein:
D, which may be different or identical, are each chosen from groups of formula:

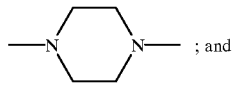 ; and

X, which may be different or identical, are each chosen from straight- and branched-chain alkylene groups comprising up to 7 carbon atoms in the main chain, optionally substituted with at least one hydroxyl group, and optionally comprising at least one substituent chosen from oxygen atoms, nitrogen atoms, sulphur atoms, aromatic rings, and heterocyclic rings, wherein said oxygen atoms, nitrogen atoms, and sulphur atoms may optionally be in the form of ether groups, thioether groups, sulphoxide groups, sulphone groups, sulphonium groups, alkylamine groups, alkenylamine groups, hydroxyl groups, benzylamine groups, amine oxide groups, quaternary ammonium groups, amide groups, imide groups, alcohol groups, ester groups or urethane groups; and (b) polymers of formula (VII'):

wherein:

D, which may be different or identical, are each chosen from groups of formula:

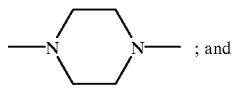

X, which may be different or identical, are each chosen from straight- and branched-chain alkylene groups comprising up to 7 carbon atoms in the main chain, optionally substituted with at least one hydroxyl group, and optionally comprising at least one substituent chosen from oxygen atoms, nitrogen atoms, sulphur atoms, aromatic rings, and heterocyclic rings, wherein said oxygen atoms, nitrogen atoms, and sulphur atoms may be in the form of an ether group, a thioether group, a sulphoxide group, a sulphone group, a sulphonium group, an alkylamine group, an alkenylamine group, a hydroxyl group, a benzylamine group, an amine oxide group, a quaternary ammonium group, an amide group, an imide group, an alcohol group, an ester group or a urethane group, wherein at least one X is chosen from straight- and branched-chain alkylene groups comprising up to 7 carbon atoms in the main chain, optionally substituted with at least one hydroxyl group, wherein said at least one X comprises at least one nitrogen atom substituted with at least one alkyl chain which may optionally be interrupted by at least one oxygen atom and which comprises at least one carboxyl group and at least one hydroxyl group and which is betainized by reaction with at least one of chloroacetic acid and sodium chloroacetate.

23. A composition according to claim 1, wherein said at least one film-forming polymer (B) is chosen from amphoteric polymers, wherein said amphoteric polymers are chosen from copolymers of (i) ($C_1$–$C_5$)alkyl vinyl ether and (ii) maleic anhydride, wherein said copolymers are partially modified by at least one of (1) semiamidation with at least one N,N-dialkylaminoalkylamine and (2) semiesterification with at least one N,N-dialkanolamine, and further wherein said copolymers may optionally further comprise at least one vinyl monomer different from said ($C_1$–$C_5$)alkyl vinyl ether monomer (i).

24. A composition according to claim 1, wherein said at least one film-forming polymer (B) is chosen from amphoteric polymers, wherein said amphoteric polymers are chosen from (1) copolymers of (i) octylacrylamide, (ii) acrylates, and (iii) butylaminoethyl methacrylate and (2) copolymers of (i) methyl methacrylate and (ii) methyl dimethylcarboxymethylammonioethyl methacrylate.

25. A composition according to claim Otto wherein said at least one film-forming polymer (B) is chosen from anionic polymers, wherein said anionic polymers are chosen from polymers of grafted silicone type comprising at least one polysiloxane portion and at least one portion comprising at least one non-silicone organic chain, wherein one portion chosen from said at least one polysiloxane portion and said at least one portion comprising at least one non-silicone organic chain forms a main chain of said at least one film-forming polymer (B) and the other portion is grafted onto said main chain.

26. A composition according to claim 1, wherein said at least one film-forming polymer (B) is chosen from polymers derived from radical polymerization of monomers:

(a) tert-butyl acrylate in an amount ranging from 50% to 90% by weight with respect to the total weight of all said monomers;

(b) acrylic acid in an amount ranging up to 40% by weight with respect to the total weight of all said monomers;

(c) at least one silicone macromer in an amount ranging from 5% to 40% by weight with respect to the total weight of all said monomers, wherein said at least one silicone macromer has the formula:

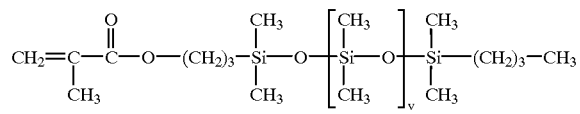

wherein v is a number ranging from 5 to 700.

27. A composition according to claim 1, wherein said at least one film-forming polymer (B) is a functionalized polyurethane, optionally comprising at least one silicone.

28. A composition according to claim 1, wherein said at least one film-forming polymer (A) is present in an amount ranging from 0.05% to 20% by weight with respect to the total weight of said composition.

29. A composition according to claim 28, wherein said at least one film-forming polymer (A) is present in an amount ranging from 0.25% to 10% by weight with respect to the total weight of said composition.

30. A composition according to claim 1, wherein said at least one film-forming polymer (B) is present in an amount ranging from 0.05% to 20% by weight with respect to the total weight of said composition.

31. A composition according to claim 1, wherein said at least one film-forming polymer (B) is present in an amount ranging from 0.25% to 10% by weight with respect to the total weight of said composition.

32. A composition according to claim 1, wherein the ratio of the concentration of said at least one film-forming polymer (A) to the concentration of said at least one film-forming polymer (B) ranges from 0.002 to 4000.

33. A composition according to claim 1, wherein said composition further comprises at least one cosmetically acceptable medium.

34. A composition according to claim 1, wherein said composition further comprises at least one cosmetic additive.

35. A composition according to claim 1, wherein said composition is in the form of a cream, a gel, an emulsion, a lotion, or a wax.

36. An aerosol device comprising at least one propellant and at least one composition comprising:

(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:

(i) a degree of elongation at break ($\epsilon_b$) of greater than or equal to 300%; and (ii) a degree of recovery at 300 seconds ($R_{300}$) of greater than or equal to 45%;

with the proviso that when said degree of recovery at 300 seconds ranges from 45% to 60%, said degree of elongation is less than 1300%; and (2) at least one film-forming polymer (B), different from said at least one polymer (A), chosen from anionic film-forming polymers, cationic film-forming polymers, and amphoteric film-forming polymers.

37. A process for holding or for shaping hair comprising applying to said hair an effective amount of a composition comprising:

(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:

(i) a degree of elongation at break ($\epsilon_b$) of greater than or equal to 300%; and (ii) a degree of recovery at 300 seconds ($R_{300}$) of greater than or equal to 45%;

with the proviso that when said degree of recovery at 300 seconds ranges from 45% to 60%, said degree of elongation is less than 1300%; and (2) at least one film-forming polymer (B), different from said at least one polymer (A), chosen from anionic film-forming polymers, cationic film-forming polymers, and amphoteric film-forming polymers.

38. A process for improving the holding or shaping power of a composition comprising including in said composition:

(1) at least one polymer (A) chosen such that a film obtained by drying a mixture of said at least one polymer (A) and at least one solvent chosen from ethanol and water, at room temperature and at a relative humidity level ranging from 45% to 55%, exhibits a mechanical profile defined by at least:

(i) a degree of elongation at break ($\epsilon_b$) of greater than or equal to 300%; and (ii) a degree of recovery at 300 seconds ($R_{300}$) of greater than or equal to 45%;

with the proviso that when said degree of recovery at 300 seconds ranges from 45% to 60%, said degree of elongation is less than 1300%; and (2) at least one film-forming polymer (B), different from said at least one polymer (A), chosen from anionic film-forming polymers, cationic film-forming polymers, and amphoteric film-forming polymers.

* * * * *

UNITED STATES PATENT AND TRADEMARK OFFICE
CERTIFICATE OF CORRECTION

PATENT NO. : 6,391,292 B1
DATED : May 21, 2002
INVENTOR(S) : Henri Samain et al.

It is certified that error appears in the above-identified patent and that said Letters Patent is hereby corrected as shown below:

Column 19,
Lines 1 though 9, formula (D),

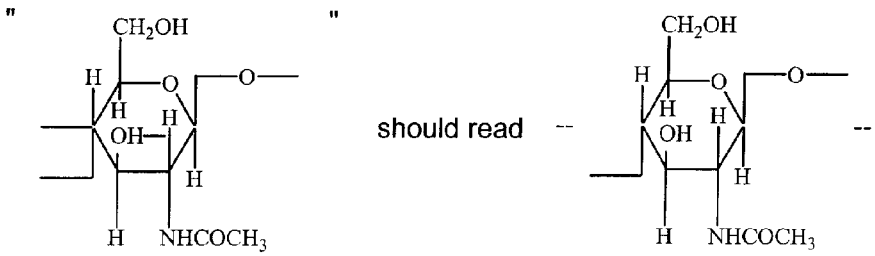

Column 19,
Line 60, after "$R_{19}$", insert a comma.

Column 20,
Line 1, after "claim", insert -- 1, --.

Column 21,
Line 65, "claim Otto" should read -- claim 1, --.

Column 22,
Line 43, "claim 1" should read -- claim 30 --.

Signed and Sealed this

Eighth Day of October, 2002

*Attest:*

*Attesting Officer*

JAMES E. ROGAN
*Director of the United States Patent and Trademark Office*